United States Patent [19]

Barberet et al.

[11] Patent Number: Plant 7,183

[45] Date of Patent: Mar. 6, 1990

[54] CARNATION NAMED LONTAKIA

[75] Inventors: Nicole Barberet; Henri Blanc, both of Antibes, France; Antonio Di Giorgio; Renato Di Giorgio, both of San Remo, Italy

[73] Assignee: Etablissements Barberet et Blanc, La Londe-Les-Maures, France

[21] Appl. No.: 315,026

[22] Filed: Feb. 24, 1989

[51] Int. Cl.[4] ..... A01H 5/00

[52] U.S. Cl. ..... Plt./71

[58] Field of Search ..... Plt./71

*Primary Examiner*—James R. Feyrer

*Attorney, Agent, or Firm*—Charles W. Rummler

[57] ABSTRACT

An original variety of standard carnation having medium sized blooms of a light pink coloration, produced profusely at recurrent intervals in Spring, Midseason and Fall, the flowers being carried on medium length, strong and erect stems, and having moderately abundant foliage. The plant itself is distinguished by its vigorous, upright and tall growth habit.

1 Drawing Sheet

BACKGROUND OF THE NEW PLANT

This carnation variety originated as a seedling at San Remo, Italy, resulting from the crossing of plants selected from our collection of carnations maintained for breeding purposes at San Remo. Our object in making this crossing was to develop new carnations having blooms of good quality and excellent color on strong plants. This plant was selected from the seedlings resulting from the said crossing because of its very extraordinary flower coloration and its apparently vigorous and strong growth habit. Propagation of the selected plant was carried on under our direction at San Remo by cuttings and in vitro propagation through several successive generations, which clearly demonstrated that the novel characteristics of its blooming and growth habits appear to be firmly fixed and would remain true from generation to generation.

Accordingly, our new carnation variety is now being propagated for commercial purposes by means of cuttings, as well as by in vitro propagation procedures, at Establissements Barberet et Blanc, Laboratoire de Physiologie Vegetale, 83250 La Londe-Les Maures, France.

DESCRIPTION OF THE DRAWING

Our new carnation variety is illustrated by the accompanying photographic drawing, which shows several blooming stems with flowers and buds in several stages of development, the color rendition being as nearly true to that herein specified as is reasonably possible to obtain by professional photographic procedures.

DESCRIPTION OF THE NEW PLANT

The following is a detailed description of our new carnation variety based upon observations made in the Spring of 1988 of plants grown in greenhouse, as well as outside, at San Remo, Italy, the color designations stated herein being according to the R.H.S. Colour Chart published by the Royal Horticultural Society of London, England.

THE PLANT

Origin: Seedling.

Parentage:

*Seed parent.*—Variety No. 141.

*Pollen parent.*—Variety No. 64.

Both parents are unpatented and unnamed and are identified in the breeding records maintained in the Di Giorgio nursery office at Via Villetta 41, 18038 San Remo, Italy.

Classification:

*Botanic.*—*Dianthus caryophyllus.*

*Commercial.*—Standard Carnation.

Form: A tall, erect bush having at least four stems emitted near the ground.

Height: Averages about 125 cm at eight months of growth.

Main stem length: Less than 15 cm due to pinching to foster branching.

Branching: This plant is branched.

Growth: Vigorous and upright.

Foliage:

*Quantity.*—Moderately abundant.

*Number of leaves.*—More than 120.

*Leaf size.*—(At the seventh node) About 16.3 cm long and about 0.72 cm wide.

*Leaf shape.*—Oblong — with curved margins.

*Texture.*—Leathery.

*Color.*—Both upper and under sides, 189-A/B.

THE BUD

Size: Large.

*Diameter.*—Averages about 2.4 cm.

*Length.*—Averages about 3.5 cm.

Shape: Ovoid.

Rate of opening: Normal.

Color of petals: When sepals first divide and petals begin to unfurl: the same as at full bloom.

Sepals:

*Number.*—Five.

*Shape.*—Generally ovoid, with acuminate tip and joined together at the lower parts.

*Character.*—The sepals are hooded over the bud before they divide and stand up when the flower opens. They are not branched.

*Color.*—Inside, 145-D; outside, between 138-A and 144-A and 145-A.

*Striae.*—Longitudinal.

Calyx:

*Shape.*—Bell-shaped.

*Size.*—Large.
*Aspect.*—Smooth.
*Splitting.*—Sometimes a little splitting occurs.
Flower stem:
*Length.*—Averages about 70 cm when cut at the tenth node.
*Character.*—Moderately rigid and erect.
*Color.*—189-A/B.

THE FLOWER

Blooming habit: Recurrent, blooming profusely in the Spring, Midseason and Fall blooming periods with a tendency to give few blooms in the Fall.
Size of flower: Medium.
*Diameter.*—Averages about 7.4 cm.
*Depth.*—Averages about 6.0 cm.
Borne: Singly, on a long, strong, upright stem.
Shape: When bloom first opens, high-centered. When bloom matures, dome-shaped.
Petalage:
*Number of petals.*—Averages about 82.
*Arrangement.*—Imbricated.
*Form.*—Fan-shaped with moderately serrated outer end margins.
*Texture.*—Leathery.
*Aspect.*—Satiny.
*Color.*—Both inner and outer petals — Body: Light Pink, 38D, 36C. Edges: 36D. Base: Greenish. Reverse Side: Light Pink, 36C/D.
Petaloids:
*Number.*—Less than ten.
*Size.*—Smaller than the petals.
*Color.*—The same as the petals.
Flower stem:

*Character.*—Upright with good strength.
Discoloration after full bloom: A little.
Persistence: The flower petals hang on and dry.
Fragrance: Perceptible.
Lasting quality: As a cut flower, at least ten days in vase keeping.

REPRODUCTIVE ORGANS

Stamens:
*Number.*—Varies from 9 to 18.
*Arrangement.*—Encircling the ovary.
*Anthers.*—Size: Less than 4 mm. Color: Yellowish White.
*Filaments.*—Length: Averages about 3.2 cm. Color: Yellowish White.
Pistils:
*Number.*—Three or four.
*Styles.*—Length: About 1.4 cm. Color: Yellowish white.
*Stigma.*—Color: Yellowish white.
Character of ovaries: Ribbed.

This carnation variety most nearly resembles the variety Lonseva (unpatented). Our new variety, however, differs from Lonseva because it has a lighter color and a wider calyx.

We claim:

1. A new and distinct standard variety of carnation plant substantially as herein shown and described, particularly distinguished by its profuse production of medium sized light pink blooms, borne on moderately long, strong, upright stems of a vigorous, rapidly growing and tall plant having moderately abundant foliage.

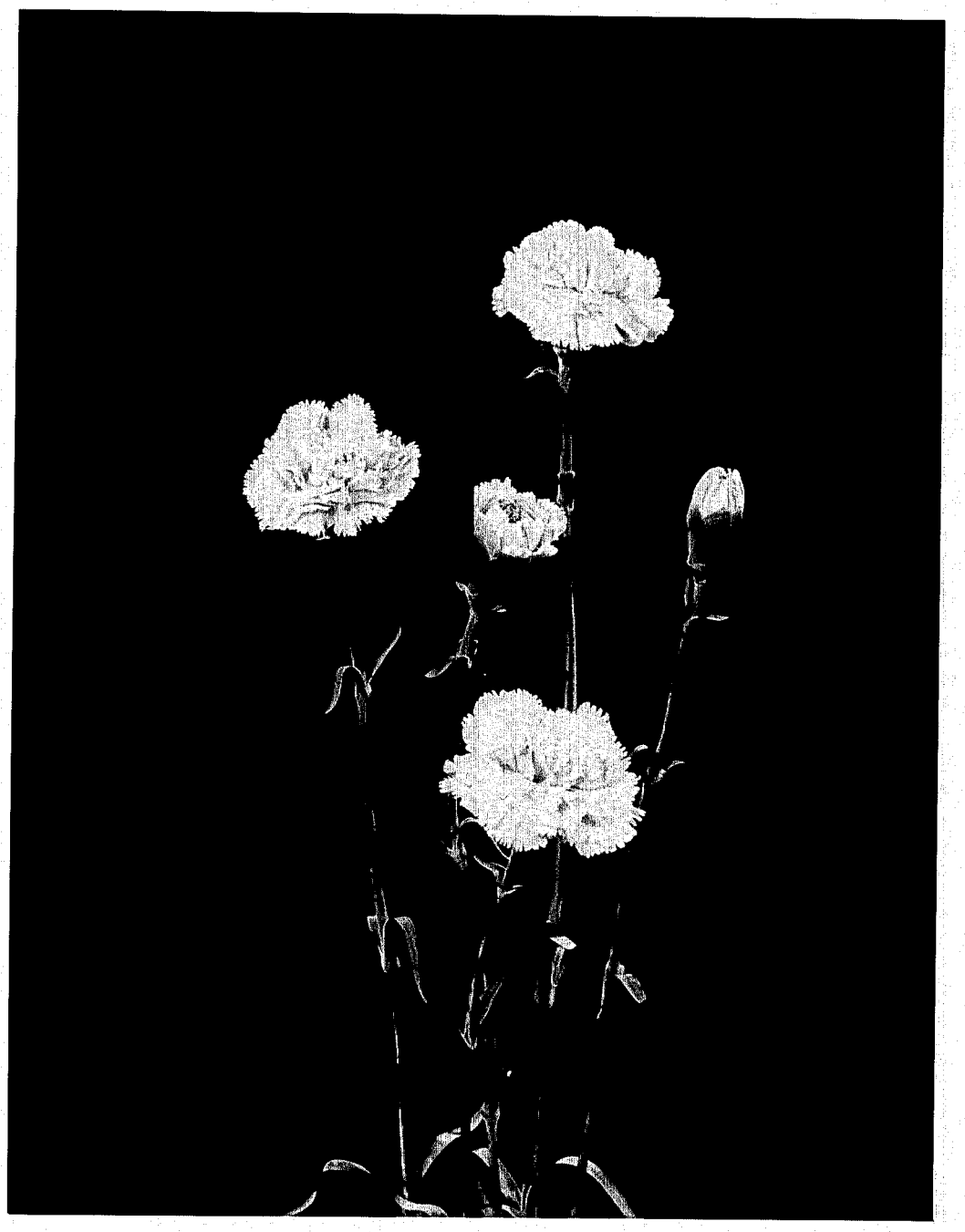

* * * * *